(12) United States Patent
Fresco

(10) Patent No.: US 9,730,845 B2
(45) Date of Patent: Aug. 15, 2017

(54) FIRST-AID KIT

(71) Applicant: Bernard Fresco, Toronto (CA)

(72) Inventor: Bernard Fresco, Toronto (CA)

(73) Assignee: Bernard Fresco, Toronto, ON (CA)

( * ) Notice: Subject to any disclaimer, the term of this patent is extended or adjusted under 35 U.S.C. 154(b) by 0 days.

(21) Appl. No.: 14/379,454

(22) PCT Filed: Feb. 14, 2013

(86) PCT No.: PCT/CA2013/000130
§ 371 (c)(1),
(2) Date: Aug. 18, 2014

(87) PCT Pub. No.: WO2013/120182
PCT Pub. Date: Aug. 22, 2013

(65) Prior Publication Data
US 2015/0027922 A1     Jan. 29, 2015

Related U.S. Application Data

(60) Provisional application No. 61/600,250, filed on Feb. 17, 2012.

(51) Int. Cl.
*A61F 17/00* (2006.01)

(52) U.S. Cl.
CPC .................................. *A61F 17/00* (2013.01)

(58) Field of Classification Search
CPC ..... A61F 17/00; A61B 19/0271; A61B 50/31; A61B 2050/311; A61J 7/0069; B65D 85/00
USPC ................................ 206/570, 438, 534, 440
See application file for complete search history.

(56) References Cited

U.S. PATENT DOCUMENTS

| | | | | | |
|---|---|---|---|---|---|
| 2,874,707 | A | * | 2/1959 | Koppel ................... | A45D 29/20 132/315 |
| 3,323,643 | A | * | 6/1967 | Rush ....................... | A61F 17/00 206/232 |
| 3,981,398 | A | * | 9/1976 | Boshoff .................. | A61F 17/00 206/232 |
| 4,553,670 | A | * | 11/1985 | Collens ................... | A61J 1/035 116/308 |
| 4,828,113 | A | * | 5/1989 | Friedland ............... | A61C 3/005 206/369 |
| 5,242,055 | A | * | 9/1993 | Pora ......................... | 206/532 |
| 5,848,700 | A | * | 12/1998 | Horn ....................... | A61F 17/00 206/459.5 |
| 5,850,630 | A | * | 12/1998 | Wilson ................ | G06F 19/3481 700/90 |

(Continued)

FOREIGN PATENT DOCUMENTS

| | | |
|---|---|---|
| GB | 2395342 A | 5/2004 |
| WO | 9851258 A1 | 11/1998 |
| WO | 0198169 A1 | 12/2001 |

OTHER PUBLICATIONS

PCT/CA2013/000130, International Search Report, Apr. 24, 2013.

*Primary Examiner* — Steven A. Reynolds
(74) *Attorney, Agent, or Firm* — Millman IP Inc.

(57) ABSTRACT

In a first aspect, the invention is directed to a first-aid kit, including a backing member, a plurality of step by step instructions arranged on the backing member, and a plurality of first-aid items, wherein each first-aid item is positioned in association with at least one of the instructions and relates to the at least one of the instructions.

10 Claims, 5 Drawing Sheets

(56) References Cited

U.S. PATENT DOCUMENTS

| | | | |
|---|---|---|---|
| 5,941,241 A * | 8/1999 | Weinstein et al. | 128/200.23 |
| 5,979,658 A * | 11/1999 | Allen et al. | 206/572 |
| 6,016,915 A * | 1/2000 | Almond | 206/570 |
| 6,112,900 A * | 9/2000 | Adkins, Jr. | 206/570 |
| 6,158,437 A * | 12/2000 | Vagley | A61B 19/0271 |
| | | | 128/898 |
| 6,187,291 B1 * | 2/2001 | Weinstein | A61J 1/00 |
| | | | 424/400 |
| 6,273,260 B1 * | 8/2001 | ColDepietro et al. | 206/532 |
| 6,571,790 B1 | 6/2003 | Weinstein | |
| 6,579,271 B1 * | 6/2003 | Aruffo et al. | 604/355 |
| 6,843,372 B2 * | 1/2005 | Weinstein | 206/534 |
| 7,398,883 B2 * | 7/2008 | Tucker | 206/570 |
| 7,967,139 B2 * | 6/2011 | Brinker | A61B 19/026 |
| | | | 206/438 |
| 8,517,989 B2 * | 8/2013 | Duncan | A61M 5/1452 |
| | | | 604/143 |
| 8,647,123 B1 * | 2/2014 | Carter et al. | 434/262 |
| 2002/0104774 A1 * | 8/2002 | Hammond | A61F 17/00 |
| | | | 206/570 |
| 2003/0196929 A1 * | 10/2003 | Gopinathan | 206/570 |
| 2003/0234198 A1 * | 12/2003 | Weinstein et al. | 206/438 |
| 2005/0230282 A1 * | 10/2005 | Lapsker | 206/570 |
| 2008/0000798 A1 * | 1/2008 | Gutmann et al. | 206/532 |
| 2009/0152137 A1 * | 6/2009 | Estes et al. | 206/232 |
| 2010/0274205 A1 * | 10/2010 | Morelli et al. | 604/290 |
| 2011/0036746 A1 * | 2/2011 | Bear | B65D 33/004 |
| | | | 206/572 |
| 2012/0152795 A1 * | 6/2012 | Leon Alonso et al. | 206/531 |
| 2012/0185276 A1 * | 7/2012 | Shah | 705/3 |
| 2013/0292294 A1 * | 11/2013 | Wilson | A61F 17/00 |
| | | | 206/571 |

* cited by examiner

FIRST-AID KIT

CROSS-REFERENCE TO RELATED APPLICATIONS

This application claims the benefit of U.S. Provisional Application No. 61/600,250, filed Feb. 7, 2012, the contents of which are incorporated herein in their entirety.

FIELD OF THE INVENTION

The present invention relates to first-aid kits.

BACKGROUND OF THE INVENTION

First-aid kits are very useful for treating injuries and the like, where the injury is relatively small and would not warrant a trip to a hospital, or where the injury is larger but would benefit from treatment quickly, (i.e. before the patient would be able to receive care from a doctor, a paramedic or the like). However, it is typical that the first-aid is carried out by a person with little or no medical training. As such these kits may or may not be provided with instructions for use in carrying out the first-aid. There is still significant opportunity for a person to apply the first-aid incorrectly using such kits however, which can result in less benefit to the injury victim than they could otherwise be provided, or which can in some situations worsen the condition of the injury victim.

SUMMARY OF THE INVENTION

In a first aspect, the invention is directed to a first-aid kit, comprising a backing member, a set of step by step instructions arranged on the backing member, and a plurality of first-aid items, wherein each first-aid item is positioned in association with at least one of the instructions and relates to the at least one of the instructions.

BRIEF DESCRIPTION OF THE DRAWINGS

The present invention will now be described by way of example only with reference to the attached drawings, in which.

DETAILED DESCRIPTION OF THE INVENTION

In many instances, when a person is injured or is otherwise in a condition requiring medical attention, carrying out a first-aid procedure on the injured person can be helpful in many ways and can in some cases help to save the life of the injured person. However, if the first-aid is carried out incorrectly it may not be as helpful as it could be, and could in some situations make the injured person's condition worse. Unfortunately, the person providing the first-aid is, in many cases, untrained medically. Additionally, the person to whom they are providing the first-aid may be known to them (e.g. a family member, a friend). In some instances the person is performing first-aid on themselves. Additionally, there may be a time sensitivity or at least a perceived time sensitivity to carrying out the first-aid procedure. All of these factors may significantly elevate the stress level of the person providing the first-aid.

Some proposed first-aid kits of the prior art include instructions on how to use the various first-aid items included in the kit, however, use of such kits is still prone to error for several reasons. Such a kit may include instructions and a number of first-aid items (multiple types of ointment, gauze, tape, etc). To use such a kit, the user must open the kit, find the instructions from amongst the first-aid items in the kit, read the instructions, and for each step of the instructions they must find the related element or elements from the kit, and then carry out that step. Unfortunately, due to the elevated stress level that may be present in the person providing the first-aid there is an increased likelihood that the person will grab and use the wrong element from the first-aid kit (e.g. the wrong ointment, the wrong drug) and could apply that wrong element to the injured person, with potentially harmful results. Also the elevated stress level in the person providing the first-aid can make them less able to carry out certain tasks quickly, such as to find something from amongst a group of things. Such errors occur periodically in high-stress environments such as an operating theatre where medical professionals sometimes pull the wrong drug from a drug storage cabinet and administer it to a patient in response to a sudden development during an operation.

Figure 1:
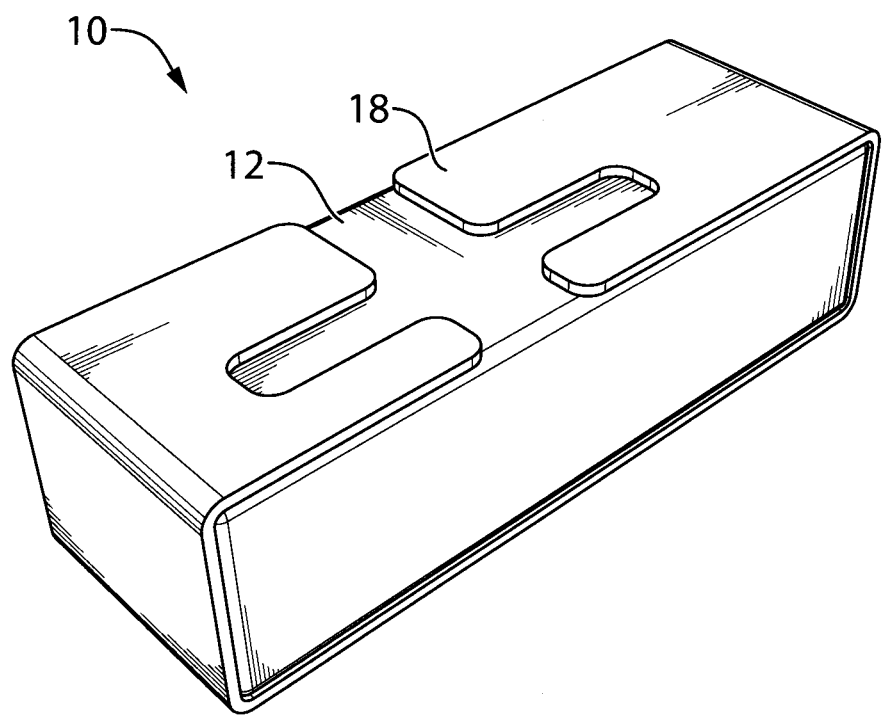
FIG. 1 is a perspective view of a first-aid kit in accordance with an embodiment of the present invention.
Figure 2A:
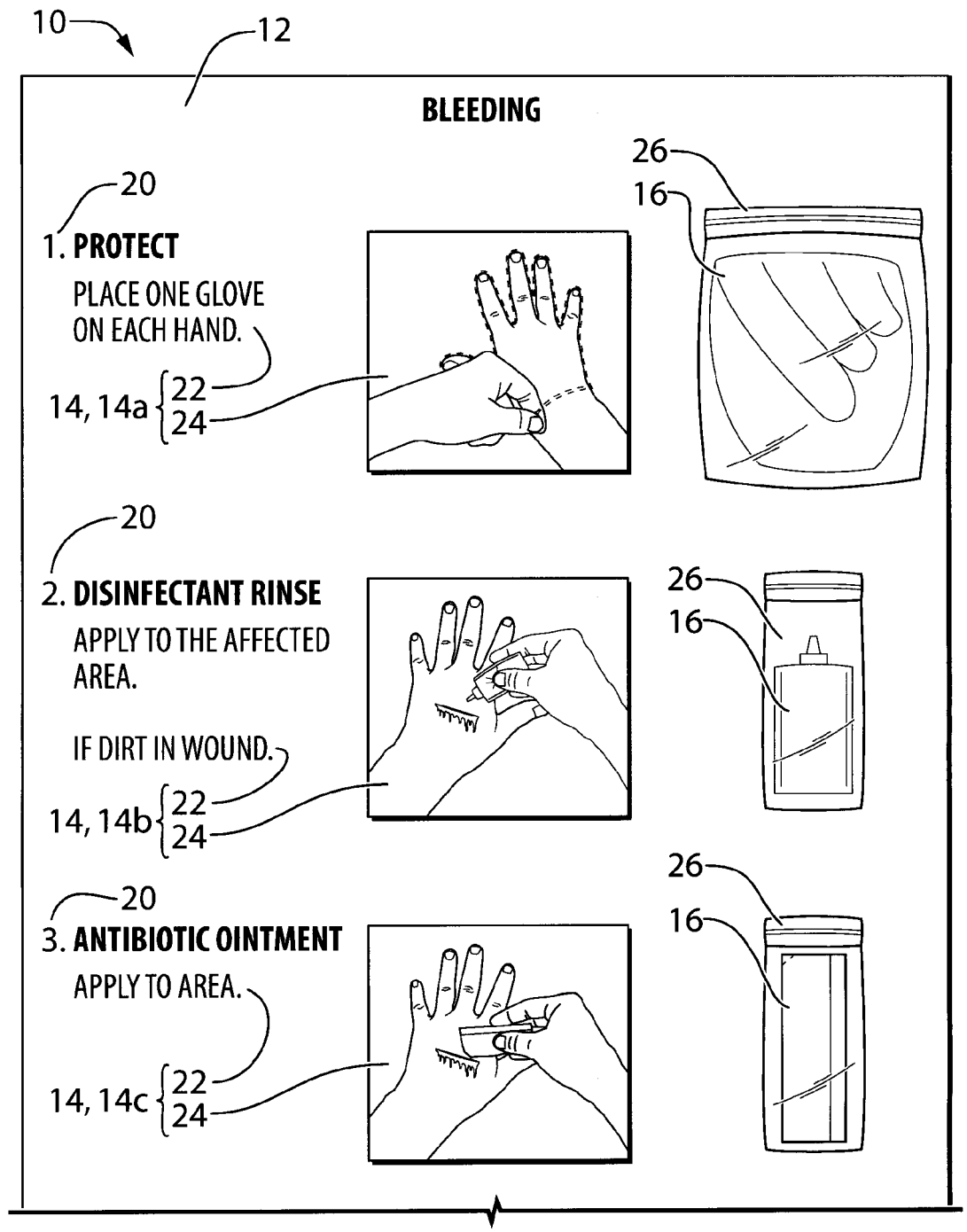
FIGS. 2a-2c are plan views of portions of a backing member with instructions and first-aid items thereon, that forms part of the first-aid kit shown in FIG. 1.
Figure 2B:
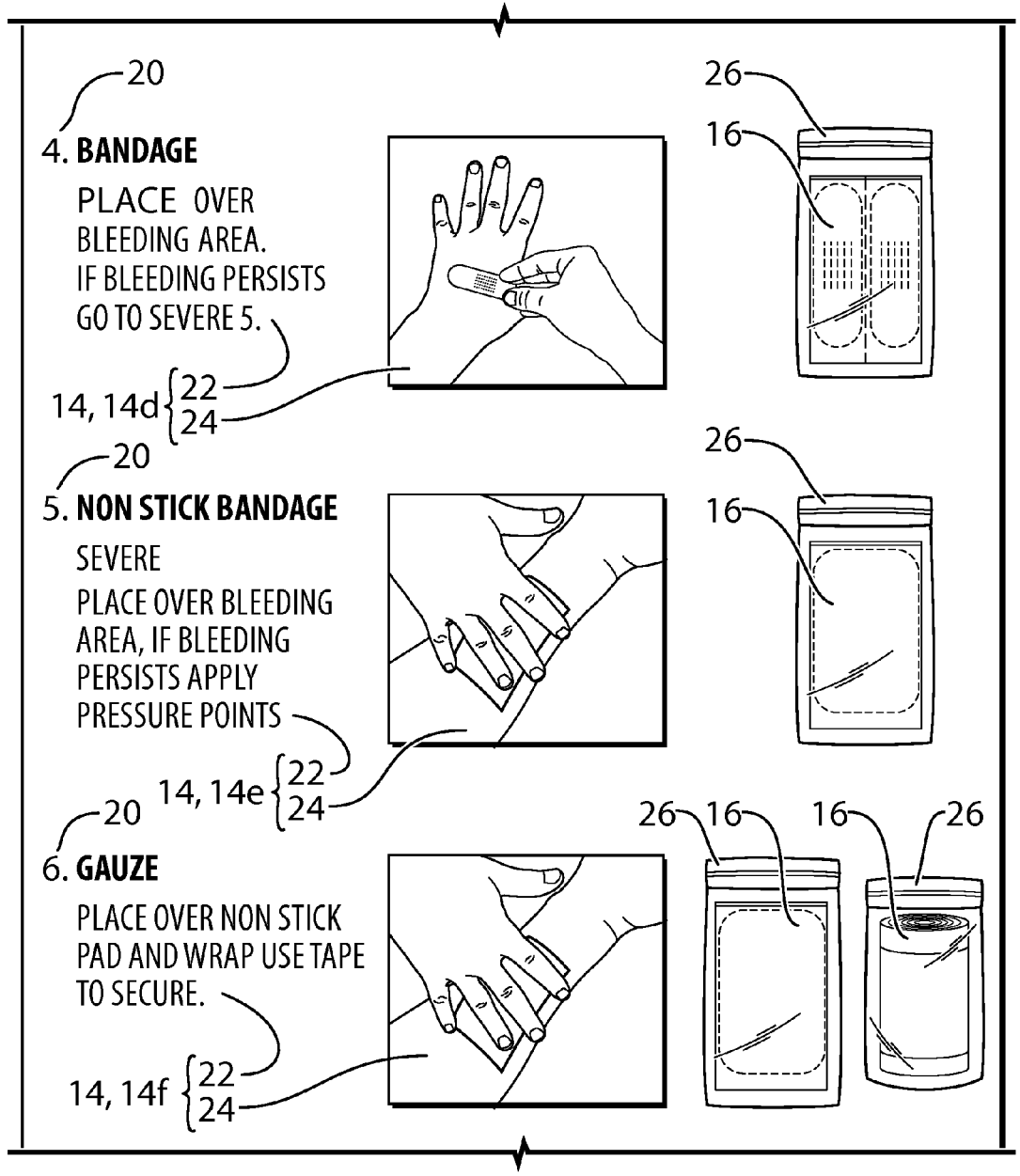
Figure 2C:
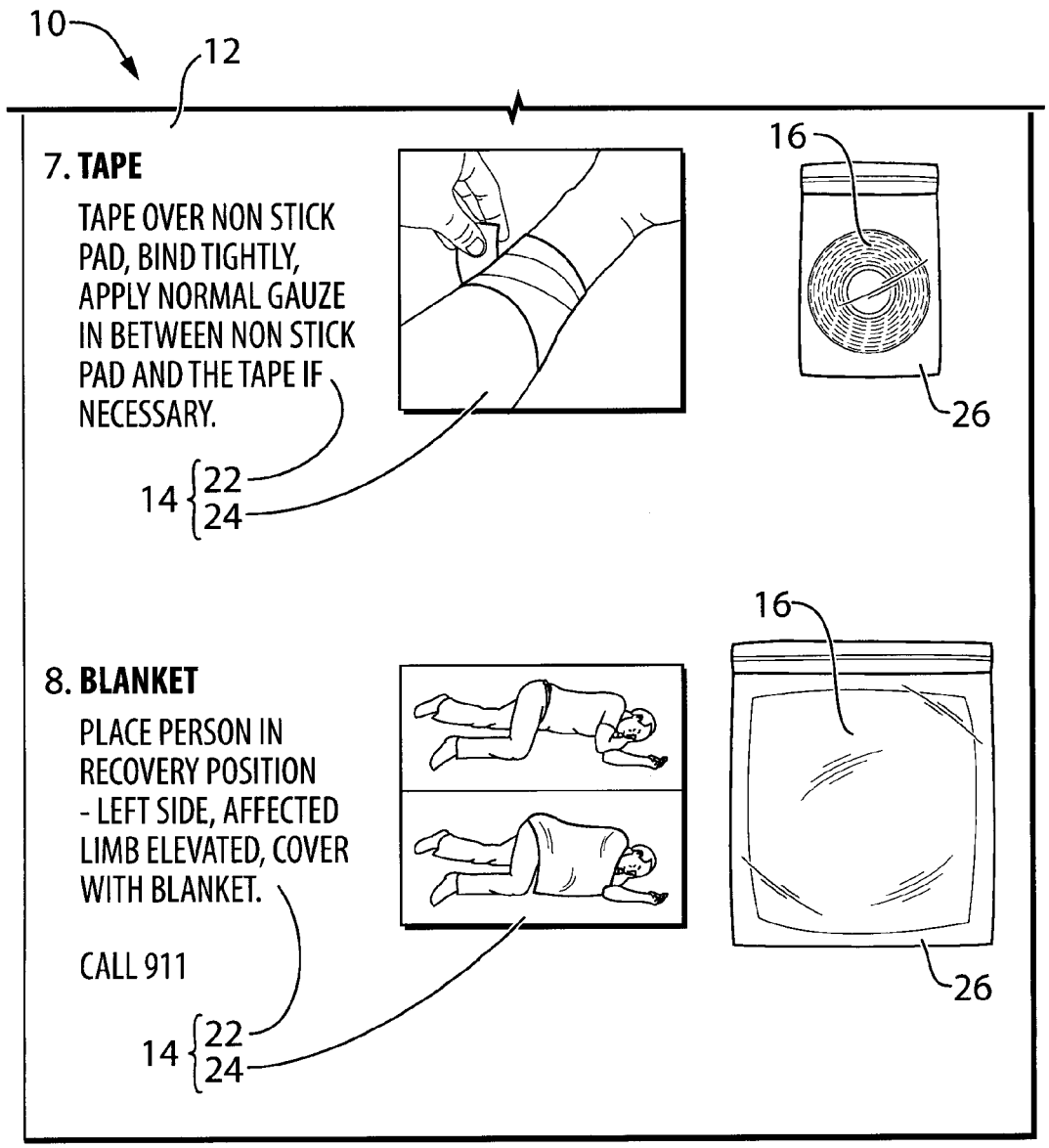

Reference is made to FIG. 1, which shows a first-aid kit 10 in accordance with an embodiment of the present invention. The first-aid kit 10 is configured to permit a person to carry out a first-aid procedure with multiple steps with a reduced likelihood of error relative to the likelihood of error that would be associated with certain prior art first-aid kits. Referring to FIGS. 2a-2c, the first-aid kit 10 includes a backing member 12, a set of step by step instructions, shown at 14, arranged on the backing member 12, and a plurality of first-aid items 16, all of which can be folded into a container 18 (shown in FIG. 1). Each first-aid item 16 is positioned in association with at least one of the instructions 14 and relates to the at least one of the instructions 14.

The backing member 12 may be a flexible sheet of material (e.g. cloth material or plastic material) and may be foldable to a storage position (FIG. 1) and openable to a use position (FIGS. 2a-2c). Instead of being a flexible member the backing member 12 could alternatively be made up of a plurality of rigid or semi-rigid members that are hingedly connected together at selected locations to permit them to fold to a storage position and open to a use position. While the backing member 12 is shown as a sheet of material in the figures, it may alternatively be configured as a frame or other open structure. Such a structure may, for example, be made up of connecting members, such as rods, that are connected to each other.

In this particular example, the first-aid kit 10 is configured for the treatment of a person who is bleeding. In other examples, the first-aid kit 10 may be configured for the treatment of burns, loss of consciousness, broken bones, hypothermia or any other suitable medical condition. To use the first-aid kit 10, a user opens the container 18 and removes the backing member 12 with the instructions 14 and first-aid items 16 thereon. The user can then open (i.e. unfold) the backing member 12 and carry out the first-aid procedure.

As shown in FIGS. 2a-2c, each instruction 14 may include one or more textual instruction elements 22 and one or more graphical instruction elements 24. For example, the instructions shown at 14a, 14b and 14c each include one textual instruction element 22 and one graphical instruction element 24. In another example, the instruction shown at 14e in FIG. 2b includes one textual instruction element 22 and two graphical textual elements 24. The textual and graphical instruction elements 22 and 24 may be positioned on the backing member 12 by any suitable means. For example, they may be printed directly on the backing member 12. Alternatively, for example, they may be printed on one large sheet or on individual sheets, whereby the one or more sheets may be joined to the backing member 12 by means of adhesive, by sewing, or by any other suitable means.

On the backing member the instructions 14 are preferably positioned in sequential order, as shown in FIGS. 2a-2c, with the first instruction shown at 14a at the top, the second instruction shown at 14b immediately subjacent to instruction 14a, the third instruction shown at 14c immediately subjacent to instruction 14b and so on. Also preferably, the instructions include indicia shown at 20 which indicate the order in which the first aid steps are to be carried out. As shown in FIGS. 2a-2c, the indicium 20 associated with instruction 14a is a 1, indicating that that is the first first-aid step to be carried out; the indicium 20 associated with instruction 14b is a 2, indicating that that is the second first-aid step to be carried out; the indicium 20 associated with instruction 14c is a 3, indicating that that is the third first-aid step to be carried out. The indicia 20 need not be numerical. The indicia may, for example, be alphabetical. In yet another embodiment, the indicia may be graphical (e.g. in the form of arrows that lead from one instruction 14 to the next).

Figure 3:
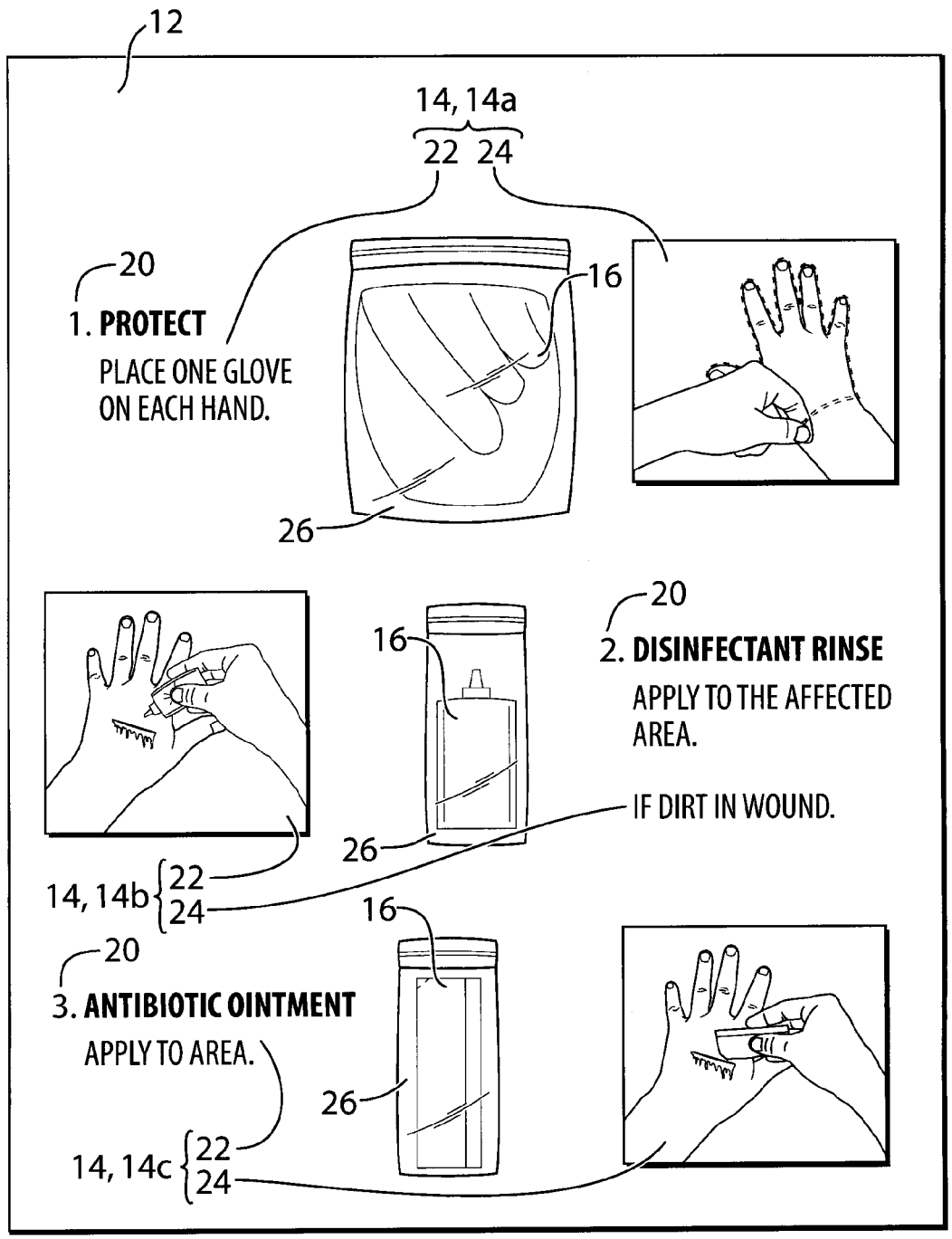
FIG. 3 is a plan view of a portion of the backing member, with the instructions and first-aid items arranged differently than those arranged in FIG. 2a-2c.

While it is preferred to have the textual instruction elements 22 aligned with each other, the graphical instruction elements 24 aligned with each other and the first-aid items 16 be aligned with each other as shown in FIGS. 2a-2c it is alternatively possible for them to not be precisely aligned with each other, as shown in the arrangement of FIG. 3. Furthermore, while it is preferred to have a consistent arrangement of the textual instruction element 22, the graphical instruction element 24 and the first-aid item 16 in each first-aid step, such as is shown in the first-aid steps identified by indicia 1-8 in FIGS. 2a-2c it is possible to have different arrangements of these elements 22, 24 and 16 in different steps, such as is shown in the first-aid steps by indicia at 1-3 in FIG. 3.

In the arrangement shown in FIG. 3 the particular arrangement of the textual and graphical instruction elements changes from instruction 14 to instruction 14, but the instructions 14 are still arranged generally in sequence. That is, the instruction 14b is positioned subjacent to instruction 14a; instruction 14c is subjacent to instruction 14c and so on. As a result, the arrangement of the instructions 14 generally provides to the user an indication of the order of the first-aid steps to be carried out. When the instructions 14 are arranged in some order, such as the vertical arrangement shown in FIGS. 2a-2c and FIG. 3, it is optionally possible to omit the indicia 20 and to rely solely on the arrangement of the instructions itself to indicate to the user the order in which the first-aid steps are to be carried out. It is alternatively possible to have the instructions 14 arranged in any desired arrangement and to rely on the indicia 20 to indicate to the user the intended order in which the first-aid steps are to be carried out.

As noted above, each first-aid item 16 is positioned in association with at least one of the instructions 14. In some embodiments, each instruction 14 has a first-aid item 16 associated with it. Alternatively, however, one or more of the instructions 14 may not have any first-aid item associated therewith. As shown in FIG. 2b, an instruction, such as, for example, instruction 14f, may have a plurality of first-aid items 16 positioned in association with it.

Each first-aid item 16 may be held in a pocket 26 on the backing member 12. The pocket 26 may be formed by any suitable means. Preferably, the pocket 26 is closable (e.g. via a flap, or via a plastic zipper as shown) to ensure that the first-aid item 16 contained therein does not fall out. Also preferably, the first-aid item 16 can be seen through the wall of the pocket 26. Alternatively, the first-aid items 16 may be held on the backing member 12 by any other suitable means.

To carry out the first-aid procedure, the user can start with the first instruction shown at 14a. In the example shown in FIG. 2a, it can be seen that the first instruction 14a instructs the user to place a glove on each hand. The first-aid item 16 positioned in association with that instruction 14a is a pair of gloves. The second instruction 14b instructs the user to apply a disinfectant to the affected area if there is dirt in the wound, using the disinfectant that is the first-aid item 16 positioned in association with the second instruction. The third instruction 14c instructs the user to apply an antibiotic ointment to the affected area, using the antibiotic ointment that is the first-aid item 16 positioned in association with the third instruction. While the antibiotic ointment and the disinfectant do appear different, it is possible that someone could have gotten one confused with the other when carrying out a first-aid procedure using a certain type of first-aid kit of the prior art. However, by positioning the disinfectant and the antibiotic ointment in association with the second and third instructions respectively, it is relatively unlikely that the user would inadvertently use one in the place of the other. As can be seen, the rest of the instructions 14 follow in FIGS. 2b and 2c.

As noted above, the instruction 14f has two first-aid items 16 associated with it however these first-aid items 16 are both involved in the carrying out of the instruction 14f.

The set of instructions 14 may contain a decision instruction which involves a decision on the part of the user, wherein the decision has multiple possible outcomes. The decision instruction 14 may branch to different subsequent instructions in the set depending on the different outcomes of the decision. For example, the instruction 14d in FIG. 2b includes a decision instruction which is: If bleeding persists (after having applied a bandage), the user is to proceed to instruction 14e. Without it being explicitly stated it will be understood that if bleeding does not persist, the user need not proceed to instruction 14e in which case there are no further steps to the first-aid procedure.

By providing the first-aid items 16 on the backing member 12 in association with the related instructions 14, the user has fewer tasks to perform as compared to some first-aid kits of the prior art. For example, the user, when using the kit 10, does not need to search through a container full of items for a particular item that is needed for a particular step. Furthermore, the user is not faced with the task of deciding which of several items that look similar is the correct one that was intended to be used at a given step in the instructions. By removing the need to perform such tasks the stress on the user of carrying out a first-aid procedure may be reduced, thereby increasing the likelihood of the procedure being carried out correctly. Furthermore, it will be noted that some time is consumed by such tasks as searching through a container for a particular item and comparing similar items to determine which is the correct one to use at a given step. By eliminating such tasks, a user can provide the first-aid more quickly than can be achieved with some kits of the prior art.

While the above description constitutes a plurality of embodiments of the present invention, it will be appreciated that the present invention is susceptible to further modification and change without departing from the fair meaning of the accompanying claims.

The invention claimed is:

1. A first-aid kit, comprising:
    a backing member;
    a set of step by step instructions arranged on the backing member, wherein the instructions are calls to action to treat a selected injury;
    a plurality of first-aid items, wherein the plurality of first-aid items are identified in the set of instructions for treating that selected injury, wherein, for at least some of the plurality of first-aid items, each first-aid item is positioned in an individual receptacle in association with at least one of the instructions and relates to the at least one of the instructions; and
    wherein, for at least some instructions in the set of step by step instructions, each instruction is positioned closer to only one of the individual receptacles than to any other one of the individual receptacles.

2. A first-aid kit as claimed in claim 1, wherein each instruction includes at least one instruction element selected from the group consisting of a textual instruction element and a pictorial instruction element.

3. A first-aid kit as claimed in claim 1, wherein each instruction includes at least one textual instruction element and at least one graphical instruction element.

4. A first-aid kit as claimed in claim 1, wherein the instructions include at least one decision instruction that identifies a selected decision to be made, the decision instruction branching to a plurality of groups of further instructions, each group being associated with a selected possible outcome of the decision.

5. A first-aid kit as claimed in claim 1, further comprising a storage container, wherein the backing member, while holding the plurality of first-aid items, folds into a storage position wherein the backing member is sized to fit within a storage container.

6. A first-aid kit as claimed in claim 1, wherein the plurality of first-aid items includes at least one of: a thermal blanket, gauze, medical tape, scissors, disinfectant rinse, antibiotic ointment, and pain relief medicine.

7. A first-aid kit as claimed in claim 1, wherein the backing member is made up of a flexible sheet of material.

8. A first-aid kit as claimed in claim 1, further comprising an indicium positioned in association with each instruction wherein the indicia indicate the order in which the instructions are to be carried out.

9. A first-aid kit as claimed in claim 1, wherein, for at least some instructions in the set of step by step instructions, each instruction is provided in a textual format and a pictorial format.

10. A first-aid kit as claimed in claim 1, wherein each receptacle is a pocket on the backing member.

* * * * *